US006695888B2

(12) United States Patent
Bartolone et al.

(10) Patent No.: US 6,695,888 B2
(45) Date of Patent: Feb. 24, 2004

(54) TRANSITION METAL COMPLEXES AS DYE FORMING CATALYSTS IN HAIR COLORING COMPOSITIONS

(75) Inventors: John Brian Bartolone, Bridgeport, CT (US); Van Au, New City, NY (US); Stephen Madison, New City, NY (US)

(73) Assignee: Unilever Home & Personal Care, USA, division of Conopco, Inc., Chicago, IL (US)

( * ) Notice: Subject to any disclaimer, the term of this patent is extended or adjusted under 35 U.S.C. 154(b) by 128 days.

(21) Appl. No.: 09/918,220

(22) Filed: Jul. 30, 2001

(65) Prior Publication Data

US 2003/0066140 A1 Apr. 10, 2003

(51) Int. Cl.[7] .................................................. A61K 7/13
(52) U.S. Cl. ........................ 8/405; 8/406; 8/410; 8/414; 8/416
(58) Field of Search ........................... 8/405, 406, 410, 8/414, 416

(56) References Cited

U.S. PATENT DOCUMENTS

| | | | | |
|---|---|---|---|---|
| 5,279,618 A | * | 1/1994 | Prota et al. ..................... | 8/406 |
| 5,873,910 A | | 2/1999 | Henrion et al. ................ | 8/406 |
| 6,004,355 A | * | 12/1999 | Dias et al. ..................... | 8/406 |

FOREIGN PATENT DOCUMENTS

| | | |
|---|---|---|
| DE | 198 52 972 A1 | 5/2000 |
| EP | 0 507 448 A2 | 10/1992 |
| WO | 97/24107 | 7/1997 |
| WO | 97/24108 | 7/1997 |
| WO | 99/33435 | 7/1999 |
| WO | 01/28508 A1 | 4/2001 |

OTHER PUBLICATIONS

Co–pending application Bartolone et al.; 10/005,950; Filed Dec. 5, 2001.
International Search Report (PCT/EP 02/07530).

* cited by examiner

Primary Examiner—Yogendra N. Gupta
Assistant Examiner—Eisa Elhilo
(74) Attorney, Agent, or Firm—Michael P. Aronson

(57) ABSTRACT

A hair coloring composition comprising a first composition which comprises:
(a) a dye forming transition metal salt or complex; which is first applied to the hair;
and a second composition which comprises the following two compositions which are mixed just prior to application to the hair:
(a) a composition comprising a water-soluble peroxygen oxidizing agent; and
(b) a composition comprising one or more oxidative hair coloring agents selected from the group consisting of an aromatic diamine, an aminophenol, a polyhydric phenol a catechol and mixtures thereof.

14 Claims, No Drawings

TRANSITION METAL COMPLEXES AS DYE FORMING CATALYSTS IN HAIR COLORING COMPOSITIONS

BACKGROUND OF THE INVENTION

The difficulties in the development of hair coloring compositions, which can deliver precise long-lasting colors with low hair damage, are in part due to the inherent structure of the hair itself and in part due to the necessary harsh conditions of effective hair coloration processes.

In general, the condition and structure of human hair is not regular along the length of the hair shaft. Human hair is subject to various chemical and mechanical treatments such as combing, brushing, shampooing, heating, perming as well as exposure to the sun. As such, the hair at the ends of the hair shaft will generally exhibit signs of damage relative to the new growth close to the scalp. This damage can lead to inconsistent coloration when the hair is dyed due to irregular uptake of the hair-coloring agents along the length of the hair shaft. Thus there is a need for hair coloring compositions which can deliver substantially consistent hair color results throughout the hair.

Once the hair has been colored there is a desire for the color to be resistant to the fading action of the sun and other exterior factors and that the color is retained in a consistent manner for a predictable period of time. Thus it would be desirable to develop a hair coloring composition which exhibited reduced fade and provided improved resistance to wash out during regular cleansing regimen. An additional difficulty commonly associated with the dyeing of human hair is the need for dye systems that avoid any adverse effect on the hair and skin of the user.

To color human or animal hair using conventional oxidative dye technology it is generally necessary to treat the hair with a mixture of suitable oxidative coloring agents and at least one oxidizing agent and swelling agent at alkaline pHs. Hydrogen peroxide is the most commonly used oxidizing agent. This can lead to undesirable hair damage. These undesirable effects are in part due to the necessary conditions of conventional peroxide treatment, as part of the hair coloring process, which requires high pH (>pH 9), use of swelling agents such as ammonia, extended exposure (from 30 to 60 minutes) and relatively high concentration of oxidizing solutions (up to 30% volume of oxygen) in order to deliver effective hair dyeing and hair melanin bleaching. Thus there is a need for hair coloring compositions, which can oxidize dye precursors and color the hair effectively without damage.

Oxidative dyes and peroxide oxidizing agents can be used to deliver a variety of hair colors to the hair. However such conventional hair coloring compositions comprising oxidative dyes and peroxide oxidizing agent do not deliver against the key consumer needs of color saturation, color vividness, precise initial color predictability, improved wash fastness, improved safety and low hair damage.

Applicants have now found that the combination of peroxide oxidizing agents with certain transition metal salts or complexes and one or more oxidative coloring agents in hair coloring compositions can deliver excellent initial hair color in a faster time, good wash fastness of the hair color over time, desirable color saturation and vividness attributes, and significantly reduced hair damage. Furthermore, applicants have found that the combination of these dye precursors and transition metal salts or complexes with a source of peroxide at particular levels and ratios in the coloring compositions of the present invention can deliver these excellent hair coloring attributes results with minimal hair damage in a faster time.

Thus it is an object of the present invention to provide improved hair coloring compositions.

The following publications relate to the field of the invention:

U.S. Pat. No. 6,004,355 discloses hair coloring compositions which comprise (a) a water-soluble peroxygen oxidizing agent, (b) an organic peroxyacid precursor oxidizing aid, and (c) one or more oxidative hair coloring agents. The compositions may be used in processes for coloring human or animal hair and may be conveniently provided in kits wherein each of the aforementioned components are individually packaged. This patent, at column 23, lines 20–35, discloses as a ligand, a list which includes 1,4,7-trimethyl-1,4,7-triazacyclononane.

WO 97/24108, WO 97/24107 and U.S. Pat. No. 6,004,355 disclose a hair bleaching composition comprising: a) a water-soluble peroxygen bleach and (b) a bleaching aid selected from organic peroxyacid bleach precursors and/or preformed organic peroxyacids. The products can provide hair bleaching and in-use efficacy benefits including reduced hair damage at lower pH.

U.S. Pat. No. 5,873,910 discloses a process for the two-stage oxidation dyeing of keratin fibers by applying to the keratin fibers:

in a first stage, at least one composition A containing at least one manganese salt and/or a manganese complex, in a second stage, at least one composition B having a pH of greater than or equal to 6, and resulting from the extemporaneous mixing of at least one composition B1 containing at least one 4-substituted 1-naphthol and at least one composition B2 containing at least one oxidizing agent, and corresponding multi-compartment dyeing kit.

This patent discloses 1,4,7-trimethyl-1,4,7-triazacyclononane as a manganese complex to be used in its process at column 10, lines 20–25.

DE 19852972 discloses the use of 1,4,7-trimethyl-1,4,7-triazacyclononane in hair dye formation.

SUMMARY OF THE INVENTION

The present invention is related to a hair coloring composition suitable for the treatment of human or animal hair. According to one aspect of the present invention, there is provided a hair coloring composition comprising a first composition which comprises:

(a) a dye forming transition metal complex; which is first applied to the hair;

and a second composition which comprises the following two compositions which are mixed just prior to application to the hair:

(a) a water-soluble peroxygen oxidizing agent; and
(b) one or more oxidative hair coloring agents selected from the group consisting of an aromatic diamine, an amino phenol, a polyhydric phenol, a catechol and mixtures thereof.

DETAILED DESCRIPTION OF THE INVENTION

As used herein, % means weight % of the total composition unless otherwise designated. The compositions of the invention are made using known ingredients or with ingredients analogous to those known in the art. The packages or containers to be used with the compositions of the invention are made using known processes and materials or by processes and materials which are analogous to those known in the art.

Compositions of the invention are used in a two step process for the coloring and bleaching of hair. That is, the first recited composition comprising dye forming transition metal catalysts is contacted with the hair, and then the second composition is made by mixing the following two ingredients just prior to application to the hair; (a) a water-soluble peroxygen oxidizing agent; and (b) one or more oxidative hari coloring agents. After mixture, this composition is then applied to hair. The coloring reaction takes place and the hair is rinsed.

As used herein the term "hair" to be treated may be "living" i.e. on a living body or may be "non-living" i.e. in a wig, hairpiece or other aggregation of non-living fibres. Mammalian, preferably human hair is preferred. However wool, fur and other melanin containing fibres are suitable substrates for the compositions according to the present invention.

The hair coloring compositions can contain, in addition to a mixture of active oxidizing agents, transition metal salts or complexes and oxidative coloring agents such as, by way of example, sequestrants, thickeners, buffers, carriers, surfactants, solvents, antioxidants, polymers non-oxidative dyes and conditioners.

As noted above, there is provided a hair coloring composition comprising a first composition which comprises:
   (a) a dye forming transition metal complex or salt;
   which is first applied to the hair; and a second composition, which comprises the following two compositions which are mixed just prior to application to the hair:
      (a) a water-soluble peroxygen oxidizing agent; and
      (b) one or more oxidative hair coloring agents selected from the group consisting of an aromatic diamine, an amino phenol, a polyhydric phenol, a catechol and mixtures thereof.

The invention also relates to a composition comprising a transition metal wherein the transition metal salt and/or transition metal complex is selected from group 1B, 6B, 7B or 8B metals and an azamacrocycle;
   a composition wherein a water-soluble peroxygen oxidizing agent is selected from hydrogen peroxide, sodium perborate, sodium percarbonate, and urea peroxide complexes;
   a composition wherein the transition metal complex is formed from a manganese salt and 1,4,7-trimethyl-1, 4,7-triazacyclononane;
   a composition wherein said manganese complex is bis (octahydro-1,4,7-trimethyl-1H-1,4,7-triazinone-N1, N4, N7)-tri-m$\mu$-oxodimanganese bis hexaflurophosphate;
   a composition wherein the weight ratio of water-soluble peroxygen oxidizing agent to transition metal complex is in the range of from about 6000:1 to about 1:2;
   a composition wherein the weight ratio of water-soluble peroxygen oxidizing agent to transition metal complex is from about 2000:1 to about 1:1;
   a composition wherein the weight ratio of water-soluble peroxygen oxidizing agent to transition metal complex is from about from 600:1 to about 60:1;
   a composition wherein the said transition metal salt and/or transition metal catalyst are present in a concentration ranging from 0.0001% to 0.2% by weight of metal equivalents relative to the total weight of composition;
   a composition wherein the said transition metal salt and/or transition metal catalyst are present in a concentration ranging from 0.001% to 0.1% by weight of metal equivalents relative to the weight of the total composition;
   a composition which further comprises a buffering agent;
   a composition having one or more oxidative hair coloring agents as described above which has a pH of about 5 to about 11;
   a composition as described above which further comprises a surfactant selected from the group consisting of anionic, nonionic, cationic, zwitterionic, amphoteric surfactants and mixtures thereof; and
   a hair coloring kit comprising an individually packaged oxidizing component with additional agents, an individually packaged component having one or more hair coloring agents and an individually packaged transition metal salt and/or transition metal complex with additional agents which when mixed forms a composition of the invention.

According to a further aspect of the present invention, there is provided a hair coloring composition comprising:
   (b) from about 0.0001% to about 2% by weight of a transition metal and a second composition which comprises the following two compositions, which are mixed just prior to application to the hair:
      (a) a composition comprising from about 0.01% to about 10% by weight of a water-soluble peroxygen oxidizing agent;
      (b) a composition comprising from about 0.0001% to about 7% by weight of one or more oxidative hair coloring agents;

The invention also relates to compositions for coloring human or animal hair wherein the hair coloring composition comprises:
   (a) a composition comprising from about 0.001% to about 1.0% by weight of a transition metal salt and/or transition metal complex;
   which is first applied to the hair; and a second composition, which comprises the following two compositions which are mixed just prior to application to the hair:
      (a) a composition comprising from about 0.5% to about 20% by weight of a water-soluble peroxygen bleaching compound
      (b) a composition comprising from about 5% to 50% additional agents selected from surfactants, buffering agents, oxidation bases and/or couplers from about 20% to about 95.5% by weight of an inert diluent The invention also relates to a process for coloring human or animal hair wherein the hair coloring composition comprises applying to the hair the compositions described above.

It has been found that compositions of the present invention are unexpectedly effective for lightening and coloring very dark brown or black hair.

For example, when (a) a dye forming transition metal complex composition of the present invention is first applied to very dark brown hair or black hair;
   and then a second composition which comprises (a) a water-soluble peroxygen oxidizing agent; and (b) a composition comprising one or more oxidative hair coloring agents the following two compositions (which are mixed just prior to application to the hair) are applied to said very dark hair brown or black hair there is obtained a very dramatic change color of the hair.

Change in hair color can be measured by means which are known in the art. A customary scale for measuring the change in hair color is defined in terms of the variables: L, a, and b wherein L, a, and b are defined as follows: L indicates the lightness or darkness of the color value. The higher the L, therefore, the lighter the hair, and the more fading that has occurred. When L is 0, the hair is black, and when L is 100, the hair is white. −a and +a represent changes in color tone from green to red. −b and +b represent the changes in color tone from blue to yellow.

What follows now is a description of the ingredients which may be used in the compositions of the invention.

Dye Forming Transition Metal Complex or Salt

The compositions of the invention comprise a transition metal containing catalyst for the peroxide oxidizing agents. One suitable type of catalyst is a catalyst system comprising a heavy metal cation of defined catalytic activity, such as copper or manganese cations, an auxiliary metal cation having little or no catalytic activity, such as zinc or aluminum cations, and a sequestrant having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 which is hereby incorporated by reference.

Other types of suitable catalysts include the manganese-based complexes disclosed in U.S. Pat. Nos. 5,246,621 and 5,244,594 which is hereby incorporated by reference.

Preferred examples of these catalysts include $Mn^{IV}_2(\mu-O)_3$(1,4,7-trimethyl-1,4,7-triazacyclononane) 2-(PF6)2, $Mn^{III}2(\mu-O)1(\mu-OAc)$ 2(1,4,7-trimethyl-1,4,7-triazacyclononane)2-(ClO$_4$)2, $Mn^{III}Mn^{IV}_4(\mu-O)_1(\mu-OAc)$ 2-(1,4,7-trimethyl-1,4,7-triazacyclononane) 2-(ClO$_4$)3, and mixtures thereof. Others are described in EP-A-0,549,272 which is hereby incorporated by reference. Other ligands suitable for use herein include 1,5,9-trimethyl-1,5,9-triazacyclododecane, 2-methyl-1,4,7-triazacyclononane, 2-methyl-1,4,7-triazacyclononane, 1,2,4,7-tetramethyl-1,4,7-triazacyclononane, and mixtures thereof.

For examples of suitable catalysts see U.S. Pat. Nos. 4,246,612 and 5,227,084 which is hereby incorporated by reference. See also U.S. Pat. No. 5,194,416 which is hereby incorporated by reference which teaches mononuclear manganese (IV) complexes such as Mn(1,4,7-trimethyl-1,4,7-triazacyclononane)(OCH$_3$)$_3$-(PF6). Still another type of suitable catalyst, is disclosed in U.S. Pat. No. 5,114,606, which is hereby incorporated by reference. It is a water-soluble complex of manganese (III) and/or (IV) with a ligand which is a noncarboxylate polyhydroxy compound having at least three consecutive C—OH groups. Other examples include binuclear Mn complexed with tetra-N-dentate and bi-N-dentate ligands, including $N_4Mn^{III}(\mu-O)_2Mn^{IV}N_4)+$ and $[Bipy2Mn^{III}(\mu-O)_2Mn^{IV}bipy2]-(ClO_4)_3$.

Further suitable catalysts are described, for example, in EP-A0,408,131 (cobalt complex catalysts), EP-A-0,384,503, and EP-A-0,306,089 which is hereby incorporated by reference (metallo-porphyrin catalysts), and U.S. Pat. No. 4,728,455 all of which are hereby incorporated by reference.

Also suitable is (manganese multidentate ligand catalyst), U.S. Pat. No. 4,711,748 and EP-A 0.224,952, (absorbed manganese on aluminosilicate catalyst), U.S. Pat. No. 4,601,845; (aluminosilicate support with manganese and zinc or magnesium salt), U.S. Pat. No. 4,626,373 (manganese ligand catalyst), U.S. Pat. No. 4,119,557 (cobalt chelant catalyst) CA-A-866,191 (transition metal containing salts), U.S. Pat. No. 4,430,243 (chelants with manganese cations and noncatalytic metal cations); and U.S. Pat. No. 4,728,455 (manganese gluconate catalysts); all of which are hereby incorporated by reference.

Other types of suitable catalysts include the manganese-based salts as described in U.S. Pat. No. 5,873,610 which is hereby incorporated by reference.

The compositions of the invention comprise one or more transition metal catalysts. When compared against a combination of all of the compositions of the invention after they have been mixed together (that is, the dye forming transition metal complex; the water-soluble peroxygen oxidizing agent composition; and the composition containing one or more oxidative hair coloring agents selected from the group) the concentration of each catalyst is from about 0.0001% to about 1% by weight and is preferably from about 0.001% to about 0.1% by weight.

The total combined level of catalysts in the compositions according to the present invention is from about 0.0001% to about 2%, preferably from about 0.001% to about 0.2%, more preferably from about 0.001% to about 0.1% by weight.

Water-Soluble Peroxygen Oxidizing Agents

The compositions of the invention may comprise at least one water-soluble peroxygen oxidizing agent. Water-soluble as defined herein means a peroxygen oxidizing agent compound, which can be substantially solubilized in water.

The peroxygen oxidizing agents useful herein are generally inorganic peroxygen materials capable of yielding hydrogen peroxide in an aqueous solution. Water-soluble peroxygen oxidizing compounds are well known in the art and include hydrogen peroxide, inorganic alkali metal peroxides such as sodium periodate and sodium peroxide and organic peroxides such as urea peroxide, melamine peroxide, and inorganic perhydrate salt oxidizing compounds, such as the alkali metal salts of perborates, percarbonates, perphosphates, persilicates, persulphates and the like. These inorganic perhydrate salts may be incorporated as monohydrates, tetrahydrates, and the like. Mixtures of two or more such oxidizing agents can be used if desired. Preferred for use in the compositions according to the present invention is hydrogen peroxide.

When compared against a combination of all of the compositions of the invention after they have been mixed together (that is, the dye forming transition metal complex; the water-soluble peroxygen oxidizing agent composition; and the composition containing one or more oxidative hair coloring agents), the peroxygen oxidizing agent is present in the compositions of the present invention at a level of from about 0.01% to about 9%, preferably from about 0.1% to about 6%, more preferably from about 0.2% to about 4% by weight.

Oxidative Hair Coloring Agents

The compositions of the present invention may include one or more oxidative hair coloring agents. Such oxidative hair coloring agents are used in combination with the oxidizing systems of the present invention to formulate permanent, hair dye compositions.

Permanent hair dye compositions as described herein are compositions, which once applied to the hair are substantially resistant to wash-out. Wash-out as described herein is the process by which hair color is removed from the hair over time during normal hair cleansing regimen.

When compared against a combination of all of the compositions of the invention after they have been mixed together (that is, the dye forming transition metal complex; the water-soluble peroxygen oxidizing agent composition;

and the composition containing one or more oxidative hair coloring agents), the concentration of each oxidative hair coloring agent is from about 0.0001% to about 7% by weight and is preferably from about 0.001% to about 2.0% by weight.

When compared against a combination of all of the compositions of the invention after they have been mixed together (that is, the dye forming transition metal complex; the water-soluble peroxygen oxidizing agent composition; and the composition containing one or more oxidative hair coloring agents), the total combined level of oxidative hair coloring agents in the compositions according to the present invention is from about 0.01% to about 15%, preferably from about 0.01% to about 10%, more preferably from about 0.1% to about 5% by weight.

Oxidative hair coloring agents which can be used in compositions of the invention can be selected from the group consisting of an aromatic diamine, an aminophenol, a polyhydric phenol, a catechol and mixtures thereof. Oxidative hair coloring agents which can also be called oxidative dyes are described in more detail below.

The dye forming intermediates used in oxidative dyes can be aromatic diamines, aminophenols and their derivatives. These dye-forming intermediates can be classified as; primary and secondary intermediates. Primary intermediates are chemical compounds, which by themselves will form a dye upon oxidation. The secondary intermediates, are also known as color modifiers or couplers and are used with other intermediates for specific color effects or to stabilize the color.

The oxidation dye intermediates which are suitable for use in the compositions and processes herein include aromatic diamines, polyhydric phenols, aminophenols and derivatives of these aromatic compounds (e.g., N-substituted derivatives of the amines, and ethers of the phenols). Primary oxidation dye intermediates are generally colorless molecules prior to oxidation. The oxidation dye color is generated when the primary intermediate is activated and subsequently joined with a secondary intermediate (coupling agent), which is also generally colorless, to form a colored, conjugated molecule.

In general terms, oxidation hair dye precursors or intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidation dye precursors capable of forming colored polymers include materials such as aniline, which has a single functional group and which, on oxidation, forms a series of conjugated imines and quinoid dimers, trimers, and the like, ranging in color from green to black. Compounds such as p-phenylenediamine, which has two functional groups, are capable of oxidative polymerization to yield higher molecular weight colored materials having extended conjugated electron systems. Color modifiers (couplers), such as those detailed hereinafter, are preferably used in conjunction with the oxidation dye precursors herein. A representative list of oxidation dye precursors suitable for use is found in Sagarin, "Cosmetic Science and Technology Interscience, Special Edn. Vol 2 pages 308 to 310, which is hereby incorporated by reference.

The typical aromatic diamines, polyhydric phenols, aminophenols, and derivatives thereof, described above as primary dye precursors can also have additional substituents on the aromatic ring, e.g. halogen, aldehyde, carboxylic acid, nitro, sulfonic acid and substituted and unsubstituted hydrocarbon groups, as well as additional substituents on the amino nitrogen and on the phenolic oxygen, e.g. substituted and unsubstituted alkyl and aryl groups.

Nonlimiting examples of suitable aromatic diamines, aminophenols, polyhydric phenols and derivatives thereof, respectively, are the following compounds:
o-phenylenediamine,
m-phenylenediamine,
2-nitro-p-phenylenediamine,
1,3,5-triaminobenzene,
2-hydroxy-p-phenylenediamine,
2,4-diaminobenzoic acid,
sodium 2,4-diaminobenzoate,
calcium di-(2,4-aminobenzoate),
ammonium 2,4-diaminobenzoate,
trimethylammonium 2,4-diaminobenzoate,
tri-(2-hydroxyethyl)ammonium 2,4-diaminobenzoate,
2,4-diaminobenzaldehyde carbonate,
2,4-diaminobenzenesulfonic acid,
potassium 2,4-diaminobenzenesulfonate,
N,N-diisopropyl-p-phenylenediamine bicarbonate,
N,N-dimethyl-p-phenylenediamine,
N-ethyl-N'-(2-propenyl)-p-phenylenediamine,
N-phenyl-p-phenylenediamine,
N-phenyl-N-benzyl-p-phenylenediamine,
N-ethyl-N'-(3-ethylphenyl)-p-phenylenediamine,
2,4-toluenediamine,
2-ethyl-p-phenylenediamine,
2-(2-bromoethyl)-p-phenylenediamine,
2-phenyl-p-phenylenediamine laurate,
4-(2,5-diaminophenyl)benzaldehyde,
2-benzyl-p-phenylenediamine acetate,
2-(4-nitrobenzyl)-p-phenylenediamine,
2-(4-methylphenyl)-p-phenylenediamine,
2-(2,5-diaminophenyl)-5-methylbenzoic acid,
2-methoxy-p-phenylenediamine,
2,3-dimethyl-p-phenylenediamine,
2,5-dimethyl-p-phenylenediamine,
2-methyl-5-methoxy-p-phenylenediamine,
2,6-methyl-5-methoxy-p-phenylenediamine,
3-methyl-4-amino-N,N-diethylaniline,
N,N-bis-(2-hydroxyethyl)-p-phenylenediamine,
3-methyl-4-amino-N,N-bis-(2-hydroxyethyl)aniline,
3-chloro-4-amino-N,N-bis-(2-hydroxyethyl)aniline,
4-amino-N-ethyl-(piperidonoethyl)aniline,
3-methyl-4-amino-N-ethyl-β-(piperidonoethyl)aniline,
4-amino-N-ethyl-N-(morpholinoethyl)aniline,
4-amino-N-ethyl-N-(acetylaminoethyl)aniline,
4-amino-N-(methoxyethyl)aniline,
3-methyl-amino-N-ethyl-N-(2-acetylaminoethyl)aniline,
4-amino-N-ethyl-N-(mesylaminoethyl)aniline,
3-methyl-4-amino-N-ethyl-N-(β-mesylaminoethyl)aniline,
4-amino-N-ethyl-N-(β-sulfoethyl)aniline,
3-methyl-4-amino-N-ethyl-N-(β-sulfoethyl)aniline,
N-(4-aminophenyl)morpholine,
N-(4-aminophenyl)piperidine,
2,3-dimethyl-p-phenylenediamine,
2-isopropyl-p-phenylenediamine,
N,N-bis-(2-hydroxyethyl)-p-phenylenediamine sulfate,
o-aminophenol,
m-aminophenol,
p-aminophenol,
2-iodo-p-aminophenol,
2-nitro-p-aminophenol,
3,4-dihydroxyaniline,
3,4-diaminophenol,
2-hydroxy-4-aminobenzoic acid,
2-hydroxy-4-aminobenzaldehyde,
3-amino-4-hydroxybenzenesulfonic acid, N,N-diisopropyl-p-aminophenol,
N-methyl-N-(1-propenyl)-aminophenol,
N-phenyl-N-benzyl-p-aminophenol sulfate,
N-methyl-N-(3-ethylphenyl)-p-aminophenol,
2-nitro-5-ethyl-p-aminophenol,
2-nitro-5-(2-bromoethyl)-p-aminophenol,
(2-hydroxy-5-aminophenyl)acetaldehyde,
2-methyl-p-aminophenol,
(2-hydroxy-5-aminophenyl)acetic acid,
3-(2-hydroxy-5-aminophenyl-1-propene,
3-(2-hydroxy-5-aminophenyl)-2-chloro-1-propene,
2-phenyl-p-aminophenol palmitate,
2-(4-nitrophenyl)-p-aminophenol,
2-benzyl-p-aminophenol,
2-(4-chlorobenzyl-p-aminophenol perchlorate,
2-(4-methylphenyl)-p-aminophenol,
2-(2-amino-4-methylphenyl)-p-aminophenol,
p-methoxyaniline,
di-(2-aminoethyl-4-aminophenyl) ether,
di-(2-hydroxyethyl-4-aminophenyl) ether,
(4-aminophenoxy)acetaldehyde,
(4-aminophenoxy)acetic acid,
(4-aminophenoxy)methanesulfonic acid,
1-propenyl-4-aminophenyl ether isobutyrate,
di-(2-chloro-1-propenyl-4-aminophenyl) ether,
di-(2-nitro-1-propenyl-4-aminophenyl) ether,
di-(2-amino-propenyl-4-aminophenyl) ether,
di-(2-hydroxy-1-propenyl-4-aminophenyl) ether,
N-methyl-p-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
2,5-dimethyl-4-aminophenol,
2-hydroxymethyl-4-aminophenol,
3-hydroxymethyl-4-aminophenol,
o-hydroxyphenol (catechol),
m-hydroxyphenol (resorcinol),
p-hydroxyphenol (hydroquinone),
4-methoxyphenol,
2-methoxyphenol,
4-(2-chloroethoxy)phenol,
4-(2-propenoxy)phenol,
4-(3-chloro-2-propenoxy)phenol,
2-chloro-4-hydroxyphenol (2-chlorohydroquinone),
2-nitro-hydroxyphenol (2-nitrohydroquinone),
2-amino-4-hydroxyphenol,
1,2,3-trihydroxybenzene (pyrogallol),
2,4-dihydroxybenzaldehyde,
3,4-dihydoxybenzoic acid,
2,4-dihydroxybenzenesulfonic acid,
3-ethyl-4-hydroxyphenol,
3-(2-nitroethyl)-4-hydroxyphenol,
3-(2-propenyl)-4-hydroxyphenol,
3-(3-chloro-2-propenyl)-4-hydroxyphenol,
2-phenyl-4-hydroxyphenol,
2-(4-chlorophenyl)-4-hydroxyphenol,
2-benzyl-4-hydroxyphenol,
2-(2-nitrophenyl)-4-hydroxyphenol,
2-(2-methylphenyl)-4-hydroxyphenol,
2-(2-methyl-4-chlorophenyl)-4-hydroxyphenol,
2-methoxy-4-(1-propenyl)phenol,
4-hydroxy-3 methoxycinnamic acid,
2,5-dimethoxyaniline,
2-methylresorcinol,
aniline,
p-chloroaniline,
p-fluoroaniline,
p-nitroaniline,
p-aminobenzaldehyde,
p-aminobenzoic acid,
sodium p-aminobenzoate,
lithium p-aminobenzoate,
calcium di-(p-aminobenzoate),
ammonium p-aminobenzoate,
p-aminobenzenesulfonic acid,
potassium p-aminobenzenesulfonate,
N-methylaniline,
N-propyl-N-phenylaniline,
N-methyl-N-2-propenylaniline,
N-benzylaniline,
N-(2-ethylphenyl)aniline,
4-methylaniline,
4-(2-bromoethyl)aniline,
2-(2-nitroethyl)aniline,
4-aminophenylacetaldehyde,
4-aminophenylacetic acid,
4-(2-propenyl)aniline acetate,
4-(3-bromo-2-propenyl)aniline,
4-phenylaniline chloroacetate,
4-(3-chlorophenyl)aniline,
4-benzylaniline,
4-(4-iodobenzyl)aniline,
4-(3-ethylphenyl)aniline,
4-(2-chloro-ethylphenyl)aniline,
phenol,
p-chlorophenol,
p-nitrophenol,
p-hydroxybenzaldehyde,
p-hydroxybenzoic acid,
p-hydroxybenzenesulfonic acid,
ethylphenyl ether,
di-(2-chloroethylphenyl) ether,
di-(2-nitroethylphenyl) ether,
phenoxyacetaldehyde,
phenoxyacetic acid,
3-phenoxy-1-propene,
3-phenoxy-2-nitro-1-propene,
3-phenoxy-2-bromo-1-propene,
4-propylphenol,
4-(3-bromopropyl)phenol,
2-(2-nitroethyl)phenol,
4-hydroxyphenylacetaldehyde,
4-hydroxyphenylacetic acid,
4-(2-propenyl)phenol,
4-phenylphenol,
4-benzylphenol,
4-(3-fluoro-2-propenyl)phenol,
4-(4-chlorobenzyl)phenol,
4-(3-ethylphenyl)phenol
4-(2-chloro-3-ethylphenyl)phenol,
2,5-xylenol,
2,5-diaminopyridine,
2-hydroxy-5-aminopyridine,
2-amino-3-hydroxypyridine,
tetraaminopyrimidine,
1,2,4-trihydroxybenzene
1,2,4-trihydroxy-5-($C_1$–$C_6$-alkyl)benzene,
1,2,3-trihydroxybenzene,
4-aminoresorcinol,
1,2-dihydroxybenzene,
2-amino-1,4-dihydroxybenzene,
2-amino-4-methoxyphenol,
2,4-diaminophenol,
3-methoxy-1,2-dihydroxybenzene,
4,6-dimethoxy-3-amino-1-hydroxybenzene,
2,6-dimethyl-4-(p-hydroxyphenyl)amino]phenol
and salts thereof.

Additional oxidation dye couplers suitable for use herein include catechol species and in particular catechol "dopa"

species which includes dopa itself as well as homologs, analogs and derivatives of DOPA. Other suitable dye precursors are dihydroxyindole (DHI), dihydroxyindolecarboxylic acid (DHICA) and derivatives thereof, indolines and derivatives thereof. Examples of suitable catechol species include cysteinyl dopa, alpha alkyl dopa having 1 to 4, preferably 1 to 2 carbon atoms in the alkyl group, epinephrine and dopa alkyl esters having 1 to 6, preferably 1 to 2 carbon atoms in the alkyl group.

The oxidation dye couplers (precursors) can be used herein alone or in combination with other oxidation dye couplers (precursors) mentioned above. The choice of a single dye coupler (precursor) will be determined by the color, shade and intensity of coloration which is desired. The following are preferred oxidation dye couplers (precursors) which can be used herein, singly or in combination, to provide oxidation hair dyes having a variety of shades ranging from ash blonde to black; these are: pyrogallol, resorcinol, p-toluenediamine, o-phenylenediamine, m-phenylenediamine, o-aminophenol, p-aminophenol, 4-amino-2-nitrophenol, nitro-p-phenylenediamine, N-phenyl-p-phenylenediamine, m-aminophenol, 2-amino-3-hydroxytoluene, N,N bis (2-hydroxyethyl)p-phenylenediamine, 4-amino-2-hydroxytoluene, 1,5-dihydroxynapthalene 2,4-diaminoanisole, hydroquinone, 4-amino-2-hydroxytoluene, 2-methyl resorcinol, 2-methyl-5-hydroxyaminophenol, 6-amino-3-hydroxy-toluene, 2,5-diaminotoluene, and 1-phenyl-3-methyl-pyazolone. These can be used in the molecular form or in the form of peroxide-compatible salts, as detailed above.

Applicant has also found that compositions of the present invention comprising particular oxidizing agents with particular transition metal salts or catalysts with oxidative dyes are valuable for the delivery of good high intensity colors with reduced levels of dye and peroxide. In particular applicant has now found that good hair coloring results can be achieved using the oxidizing systems of the present invention and up to about 84% less dye versus conventional hair coloring compositions. As such the compositions according to the present invention are valuable for the delivery of good initial color and wash fastness over time in addition to having low hair damage attributes.

Solvents

Water is the preferred principal diluent for the compositions according to the present invention. As such, the compositions of present invention may also include one or more solvents as additional diluent materials. Generally, the solvent is selected to be miscible with water and innocuous to the skin. Solvents suitable for use herein include $C_1$–$C_{20}$mono- or polyhydric alcohols and their ethers, glycerine, with monohydric and dihydric alcohols and their ethers preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and mixtures thereof.

The compositions of the invention may also include the following materials.

Buffering Agents

The coloring compositions of the present invention may have a pH in the range of from about 5 to about 11, more preferably from about 6 to about 8, and especially from about 6 to about 7.

As herein before described the preferred coloring compositions of the present invention may contain one or more buffering agents and/or hair swelling agents (HSAs) to adjust the pH to the desired level. Several different pH modifiers can be used to adjust the pH of the final composition or any constituent part thereof.

Thickeners

The composition containing one or more oxidative hair coloring agents of the present invention (coloring compositions) may additionally include a thickener at a level of from about 0.05% to about 20%, preferably from about 0.1% to about 10%, more preferably from about 0.5% to about 5% by weight. Thickening agents suitable for use in the compositions of the invention may be selected from the group consisting of oleic acid, cetyl alcohol, oleyl alcohol, sodium chloride, cetearyl alcohol, stearyl alcohol, and synthetic thickeners; and mixtures thereof.

Surfactant Materials

The compositions of the present invention may additionally contain a surfactant system. Suitable surfactants for inclusion in the compositions of the invention generally have a lipophilic chain length of from about 8 to about 22 carbon atoms and can be selected from the group consisting of anionic, cationic, nonionic, amphoteric, zwitterionic surfactants and mixtures thereof.

Materials used in compositions of the invention may be employed in the following ranges:

Hair Coloring Composition

EXAMPLE 1
(Which Shows Ranges of Ingredients)

| | |
|---|---|
| Oxidative dyes | 0.01–15 |
| Sequestrant | 0.01–1 |
| Antioxidant | 0.01–3 |
| Solvent | 2.0–35 |
| Buffering agent | 0.01–10 |
| Thickener | 0.05–20 |
| Surfactants | 5.0–40 |
| Water to | 100 |

Ranges of Ingredients which can be Included in Hair Coloring Compositions of the Invention EXAMPLE 2
(Which Shows Ranges of Ingredients)

| | | |
|---|---|---|
| p-Phenylenediamine | Oxidative dyes | 0.0001–7 |
| 4-Amino-2-Hydroxytoluene | Oxidative dyes | 0.0001–7 |
| p-Aminophenol | Oxidative dyes | 0.0001–7 |
| 2-Methylresorcinol | Oxidative dyes | 0.0001–7 |
| Phenyl-methyl-pyrazolone | Oxidative dyes | 0.0001–7 |
| N,N-bis-2-hydroxyethyl-PPD sulfate | Oxidative dyes | 0.0001–7 |
| 3-Methyl-4-aminophenol | Oxidative dyes | 0.0001–7 |
| Sodium sulphite | Antioxidant | 0.01–3 |
| Sodium EDTA | Sequestrant | 0.01–1 |
| Sodium isoascorbate | Antioxidant | 0.01–3 |
| Propylene glycol | Solvent | 2.0–35 |
| Oleic acid (5 Titre) | Buffering agent | 0.01–10 |
| Isopropanol | Solvent | 2.0–35 |
| Perfume oil | Fragrance | 0.1–1 |
| Dihydroxyethyl soyamine dioleate | Surfactants | 5.0–40 |
| PEG3 Cocamine | Surfactants | 5.0–40 |
| Water | | balance |

As used here in PPD means p-phenylene-diamine.

Ranges of ingredients which can be Included in Catalyst Compositions of the Invention

| | |
|---|---|
| 1,4,7-trimethyl-1,4,7-triazacyclononane tri-$\mu$-oxo-manganese complex | 0.0001–1 |
| Water | To balance |

EXAMPLE 3
(Which Shows Ranges of Ingredients)

| Chemical Name | % (w/w) |
|---|---|
| Sequestrant | 0.01–1 |
| Antioxidant | 0.01–3 |
| Solvent | 2.0–35 |
| Buffering agent | 0.01–10 |
| Thickener | 0.05–20 |
| Surfactants | 5.0–40 |
| Oxidizing agent | 0.01–9 |
| Water to balance | 100 |

EXAMPLE 4
(Which Shows Ranges of Ingredients)

| Chemical Name | % (w/w) |
|---|---|
| Catalyst Formulation (or transition metal salt or complex formulation) | |
| Catalyst | 0.0001–1 |
| Solvent | q.s. |
| Developer formulation | |
| Oxidizing agent | 0.01–9 |
| Water to balance | to 100 |

The following is example 5 is a specific example of a composition of the invention that was made.

EXAMPLE 5

| Ingredients | Wt % |
|---|---|
| p-Phenylenediamine | 0.05 |
| 4-Amino-2-hydroxytoluene | 0.0172 |
| p-Aminophenol | 0.2 |
| 2-Methylresorcinol | 0.3 |
| Phenyl-methyl-pyrazolone | 0.02 |
| N,N-bis-2-hydroxyethyl-PPD sulphate | 0.001 |
| 3-methyl-4-aminophenol | 0.006 |
| Sodium sulphite | 1 |
| Sodium isoascorbate | 0.15 |
| propylene glycol | 8.6 |
| Oleic acid | 8.6 |
| Isopropanol | 12.5 |
| Perfume oil | 0.5 |
| Dihydroxyethyl soyamine dioleate | 22.2 |
| PEG3 cocamine | 8 |
| Water | q.s |

EXAMPLE 6

| Developer Formulation which includes the water-soluble peroxygen oxidizing agent | |
|---|---|
| Chemical Name | % (w/w) |
| Ceteareth-7 | 1 |
| Polyquaternium 37 | 1 |
| 50% Hydrogen peroxide | 12 |

| -continued | |
|---|---|
| Developer Formulation which includes the water-soluble peroxygen oxidizing agent | |
| Chemical Name | % (w/w) |
| 85% Phosphoric acid | 0.03 |
| Water to balance | 100 |

| Dye forming transition metal complex which is a Manganese Catalyst Formulation | |
|---|---|
| Chemical Name | % (w/w) |
| Surfactant | 1 |
| 1,4,7-trimethyl-1,4,7-triazacyclononane tri-$\mu$-oxo-manganese complex | 0.1 |
| Water to balance | 100 |

Preparation of dye composition—that is, the composition which comprises oxidative hair coloring agents:

Buffering agent, surfactants, perfume oil and solvent are mixed at 55° C. to obtain a homogenous solution (part 1). Deionized water is added to the beaker and mixing is continued. Antioxidants are added followed by solvent and nitrogen blanketing is begun. Dyes are added and the mixture is heated to 50–55° C. and further mixed until the solution is clear. The solution is cooled to 40–45° C. and more water is added.

Preparation of Dye Forming Transition Metal Complex

Add deionized water to beaker and begin mixing. Add surfactants, and thickener followed by catalyst and remaining ingredients to water.

Preparation of water-soluble peroxygen oxidizing agent formulation which is also known as developer formulation:

Add deionized water to beaker and begin mixing. Add surfactants, thickener and buffering agents follow by oxidizing agent and remaining ingredients to water.

How to Use Compositions of the Invention

As described above, a first composition of the invention comprises:

(a) a dye forming transition metal salt or complex.

As described above a second composition of the invention comprises a mixture of the following two compositions:

(a) a water-soluble peroxygen oxidizing agent; and (b) one or more oxidative hair coloring agents selected from the group consisting of an aromatic diamine, an amino phenol, a polyhydric phenol, a catechol and mixtures thereof.

The hair to be colored can first be made wet with water. Then a dye forming transition metal salt or complex as described above, can be applied to the hair. Application temperatures may be in the range from 15 to 40 degrees C. Then a water-soluble peroxygen oxidizing agent; and one or more oxidative hair coloring agents as described above, are thoroughly mixed together, and soon after, this mixture is applied to the hair. Again application temperatures may be in the range from 15 to 40 degrees C. After a contact time of about 5 to about 30 minutes, the hair is thoroughly rinsed.

While the invention has been described in connection with preferred embodiments, this description is not intended to limit the invention to the particular embodiments set forth. To the contrary, this description is intended to cover such alternatives, modifications, and equivalents as may be included within the spirit and scope of the invention as defined by the appended claims.

What is claimed is:

1. A composition for coloring hair which comprises a first composition comprising:
   (a) manganese catalyst selected from the group consisting of a salt or complex formed between manganese and an azamacrocycle; a manganese multidentate ligand catalyst; an absorbed manganese on aluminosilicate catalysts; manganese gluconate catalysts; manganese based salts, and mixtures thereof;

and a second composition which comprises the following two compositions which are mixed just prior to application to the manganese catalyst-treated hair:
   (a) a composition comprising a water-soluble peroxygen oxidizing agent selected from the group consisting of hydrogen peroxide, sodium perborate, sodium percarbonate sodium and urea peroxide complexes; and
   (b) a composition comprising one or more oxidative hair coloring agents selected from the group consisting of an aromatic diamine, an aminophenol, a polyhydric phenols, a catechol and mixtures thereof, wherein the first composition comprising the manganese catalyst is applied to the hair before the second composition.

2. A composition according to claim 1 wherein the azamacrocycle is 1,4,7-trimethyl-1,4,7-triazacyclononane.

3. A composition according to claim 1, wherein said manganese catalyst is bis(octadydro-1,4,7-trimethyl-1H-1,4,7-troazinone-N1,N4,N7)-tri-m $\mu$-oxodimanganese bis hexafluorophosphate.

4. A composition according to claim 1 wherein the weight ratio of the water-soluble peroxygen oxidizing agent to the manganese catalyst is in the range of from about 6000:1 to about 1:2.

5. A composition according to claim 1, wherein the weight ratio of the water-soluble peroxygen oxidizing agent to the manganese catalyst is in the range of from about 2000:1 to about 1:1.

6. A composition according to claim 1, wherein the weight ratio of the water-soluble peroxygen oxidizing agent to manganese catalyst is in the range of from about 600:1 to about 60:1.

7. A composition according to claim 1, wherein the manganese catalyst is present in a concentration ranging from about 0.0001% to about 0.2% by weight of metal equivalents relative to the weight of the total composition.

8. A composition according to claim 1, wherein the manganese catalyst is present in a concentration ranging from about 0.001% to about 0.1% by weight of metal equivalents relative to the weight of the total composition.

9. A composition according to claim 1, in which the composition comprising one or more oxidative hair coloring agents further comprises a buffering agent.

10. A composition according to claim 9, which has a pH of about 5 to about 11.

11. A composition according to claim 1, which further comprises a surfactant selected from the group consisting of anionic, nonionic, cationic zwitterionic, amphoteric surfactants and mixtures thereof.

12. A process for coloring human or animal hair which comprises first applying to said hair a composition comprising
   (a) form about 0.001% to about 1.0% by weight of a manganese catalyst selected from the group consisting of a salt or complex formed between manganese and an azamacrocycle; a manganese multidentate ligand catalyst; an absorbed manganese on aluminosilicate catalysts; a manganese gluconate catalysts; a manganese multidentate ligand catalyst; a manganese based salts, and mixtures thereof; and then applying to said hair, a second composition which comprises the following two compositions which are mixed just prior to said second application to the hair:
   (a) a composition comprising from about 0.5% to about 20% by weight of a water-soluble peroxygen oxidizing agent selected from the group consisting of hydrogen peroxide, sodium perborate, sodium percarbonate sodium and urea peroxide complexes; and
   (b) a composition comprising one or more oxidative hair coloring agents selected from the group consisting of an aromatic diamine, an aminophenol, a catechol and mixtures thereof, wherein the hair is not rinsed between the application of the first catalyst composition and the second oxidative dye/developer composition, and wherein the composition comprising one or more oxidative hair coloring agents has a pH of from about 5 to about 11.

13. A process for lightening and coloring very dark or black hair which comprises first applying to said hair a composition comprising:
   (a) a manganese catalyst selected from the group consisting of a salt or complex formed between manganese and an azamacrocycle; a manganese multidentate ligand catalyst; an absorbed manganese on aluminosilicate catalysts; manganese gluconate catalysts; manganese multidentate ligand catalyst; manganese based salts, and mixtures thereof; and then applying to said hair, without rinsing a second composition which comprises the following two compositions which are mixed just prior to said second application to the hair:
   (a) a composition comprising from about 0.5% to about 20% by weight of a water-soluble peroxygen oxidizing agent selected from the group consisting of hydrogen peroxide, sodium perborate, sodium percarbonate sodium and urea peroxide complexes; and
   (b) a composition comprising one or more oxidative hair coloring agents selected from the group consisting of an aromatic diamine, an aminophenol, a catechol and mixtures thereof, wherein the hair is not rinsed between the application of the first catalyst composition and the second oxidative dye/developer composition, and wherein the composition comprising one or more oxidative hair coloring agents has a pH of from about 5 to about 11.

14. A hair coloring kit comprising an individually packaged oxidizing component, an individually packaged component having one or more hair coloring agents, and an individually packaged manganese catalyst component and written direction to first apply the manganese catalyst component, mix the oxidizing and coloring components and applying this mixture to the catalyst treated hair without rinsing and, and finally rinsing the hair, wherein said components are compositions in accordance with claim 1.

* * * * *